United States Patent [19]

Margaronis et al.

[11] Patent Number: 4,556,991
[45] Date of Patent: Dec. 10, 1985

[54] PROTECTING VEIL FOR WELDING HELMETS

[76] Inventors: Mihail A. Margaronis, 167 Parkview Ave., Bangor, Mass. 04401; Richard L. Manzo, 54 Prospect St., Millinocket, Me. 04462

[21] Appl. No.: 648,072

[22] Filed: Sep. 7, 1984

[51] Int. Cl.⁴ .............................................. A42B 3/00
[52] U.S. Cl. ........................................ 2/8; 2/185 R; 2/199; 2/207
[58] Field of Search ................... 2/8, 9, 207, 185 R, 2/199

[56] References Cited

U.S. PATENT DOCUMENTS

| | | | |
|---|---|---|---|
| 1,239,910 | 9/1917 | Harris | 2/185 R |
| 2,354,502 | 7/1944 | Cockrill et al. | 2/8 |
| 2,688,962 | 9/1954 | Summers. | |
| 2,882,894 | 4/1959 | Fahey et al. | |
| 4,172,294 | 10/1979 | Harris | 2/171.3 |

FOREIGN PATENT DOCUMENTS 1154740  6/1969  United Kingdom ............... 2/8

OTHER PUBLICATIONS

Rite Whitecap (TM) P.N.R. #1117.

*Primary Examiner*—Louis K. Rimrodt
*Attorney, Agent, or Firm*—Daniel H. Kane, Jr.

[57] ABSTRACT

Apparatus is described for protecting a welder in association with a standard welding helmet of the type which is open at the top and back of the helmet. An elongate flexible veil comprising fire resistant fabric material is provided having a width across the top sufficient to match the width of the welding helmet. The veil is formed with shoulder length for extending from the helmet edge contour across the top of the helmet over the back of the helmet and below the bottom of the helmet a sufficient distance so that the bottom of the veil lies on the back of the shoulders of a welder wearing the welding helmet.

7 Claims, 4 Drawing Figures

PROTECTING VEIL FOR WELDING HELMETS

TECHNICAL FIELD

This invention relates to apparatus for protecting a welder and in particular to a new protective attachment for standard welding helmets.

BACKGROUND ART

Conventional welding helmets or hoods are generally formed with a molded plastic or fiber glass face cover with a dark glass viewing port in the front. The welding helmet is open at the top and the back and provides no protection from the arc welding rays, sparks, slag and spatter from other welders who may be operating above or behind. Arc welding rays or even sunlight can enter the helmet from behind and reflect off the dark glass of the viewing port into the eyes of the welding operator. A recurring problem with the standard helmets is that the sparks, slag and spatter from a welding operation can also enter the helmet from behind or fall directly on the back of the head, neck or collar of the welder.

A variety of head enclosing hoods and shields have been devised for protecting workmen under hazardous conditions. The Cockrill et al. U.S. Pat. No. 2,354,502, the Summers U.S. Pat. No. 2,688,962, the Fahey et al. U.S. Pat. No. 2,882,894, and the Harris U.S. Pat. No. 4,172,294 are representative of such head shields, helmets and hoods which effectively fully enclose the head of a workman. Another example of a helmet or hood enclosure is the WHITECAP (TM) Protective Unit for industrial and agricultural employees who work in hazardous or uncomfortable areas manufactured by Personal Environment Systems.

A disadvantage of such protective enclosures is that air circulation around the worker's face and head is cut off and a separate air hose and air supply must be provided for the hood or helmet. Sound transmission is also cut off and the worker cannot respond to environmental sounds creating new safety hazards. Furthermore, the increased weight and material of the enclosing hoods and helmets impede worker mobility increase working temperatures inside the helmet and require substantially greater expense. Finally, the full helmet or hood enclosure must be worn under all circumstances whether required or not.

OBJECTS OF THE INVENTION

It is therefore an object of the present invention to provide a new protective attachment for use in association with standard welding helmets which is readily removable and replaceable and may be secured to the conventional welding helmet for protecting the top of the head, back of the head and neck of the welder.

Another object of the invention is to provide a relatively lightweight flexible protective attachment for retrofitting standard welding helmets which may be folded to a small size and carried by the worker for rapid deployment and use according to the environmental conditions and which also may be easily removed and stored.

A further object of the invention is to provide a protective attachment for welding helmets which does not interfere in the circulation of air or transmission of sound through and inside the helmet but which also effectively protects the welder from arc welding rays, sparks, and spatter and from other environmental factors such as sunlight glare and rain or other precipitation.

DISCLOSURE OF THE INVENTION

In order to accomplish these results the invention provides an elongate flexible fabric veil comprising fire resistant fabric material having a width across the top sufficient to match the width of the welding helmet. The elongate veil is formed with shoulder length for extending from the helmet edge contour across the top of the helmet over the back of the helmet and below the bottom of the helmet a sufficient distance so that the bottom of the veil lies on the back of the shoulders of a welder wearing the welding helmet.

According to the invention the veil is constructed and tapered with increasing width in the elongate direction along the sides of the veil from the veil top edge to the bottom of the veil. The veil bottom edge is formed to be substantially wider than the helmet for spreading out on either side behind the helmet across the back of the shoulders of a welder wearing the helmet. A feature and advantage of this configuration is that the veil thereby deflects arc rays, light rays, and welding spatter coming from behind or above the welder thereby shielding the welder from entry of rays or spatter into the helmet from behind. The invention also provides an engaging coupling surface across the veil top edge and a complementary coupling surface constructed and arranged to be secured to the helmet at the helmet edge contour on the outside surface of the helmet across the top of the helmet. The engaging coupling surface across the veil top edge is secured to the helmet along the complementary coupling surface at the helmet edge contour on the outside surface of the top of the helmet. The veil is therefore secured to the helmet only across the top of the veil without the sides of the veil being secured to the helmet.

A feature and advantage of this arrangement is that the veil, according to the present invention, provides elongate side openings oriented in the forward direction between the helmet and the veil on a welder wearing the helmet. The elongate side openings permit free movement of the veil relative to the back of the shoulders of a welder during movement of the welder's head and during raising and lowering of the helmet. At the same time the veil protects the back of the head, neck and collar of the welder shielding and deflecting rays and spatter from above and behind. At the same time the veil configuration of the invention permits free air movement and movement of sound waves through the helmet at the side openings between the helmet and veil.

A further feature of the invention is that the veil is easily and readily removable and replaceable with respect to the welding helmet and foldable and portable so that a welder can conveniently carry the veil in folded condition in a small space for ready use according to the environmental conditions at the work place.

Other objects, features and advantages of the invention are apparent in the following specification and drawings.

DESCRIPTION OF PREFERRED EXAMPLE EMBODIMENT AND BEST MODE OF THE INVENTION

Figure 1:
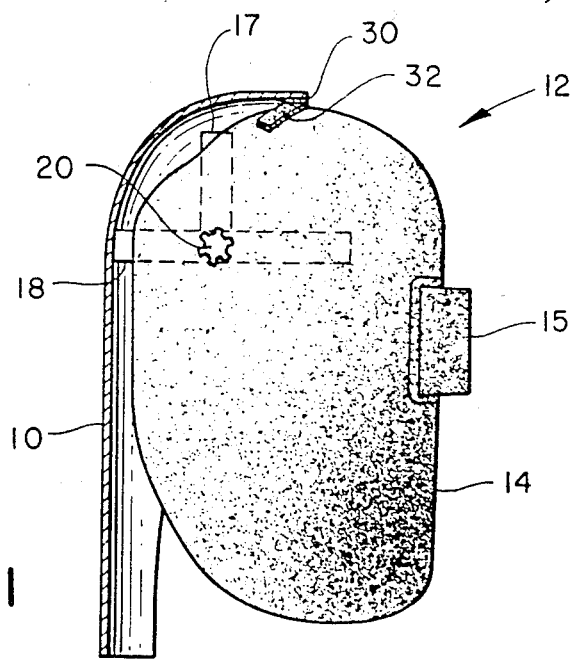
FIG. 1 is a side view of a standard welding helmet and a side cross sectional view of the protective veil mounted on and secured to the welding helmet in accordance with the present invention.
Figure 3:
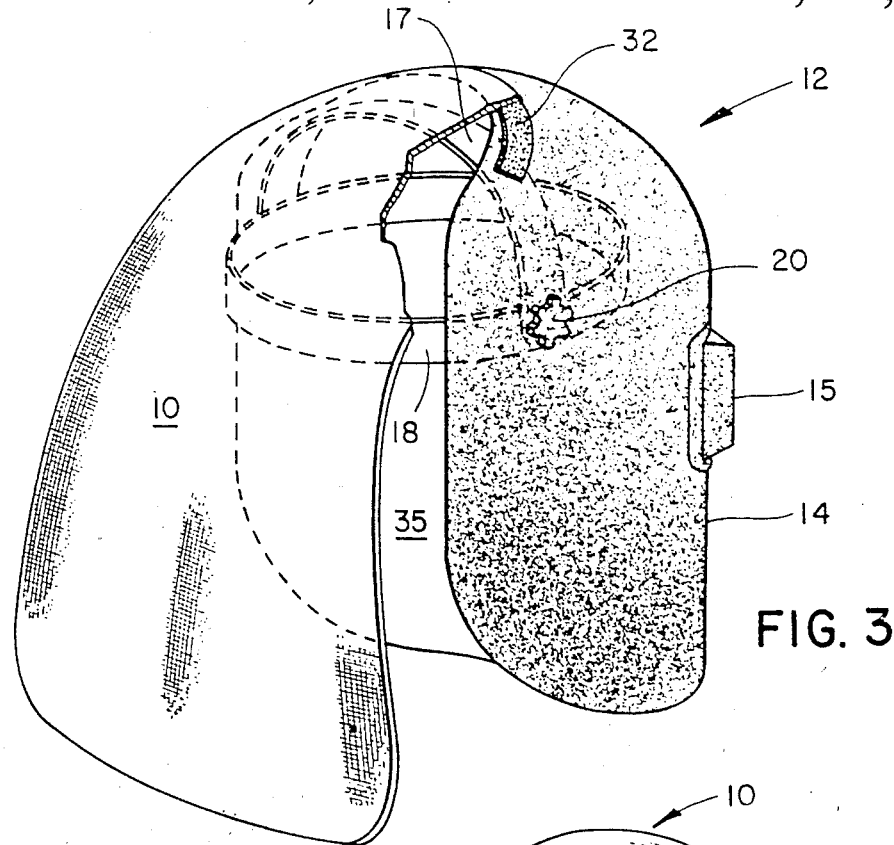
FIG. 3 is a perspective view from the rear quarter of the protective veil and welding helmet with the veil or flap partially cut away showing the helmet edge contour across the top of the helmet and the complementary coupling surfaces securing the veil top edge at the helmet edge contour on the outside surface of the helmet across the top.
Figure 4:
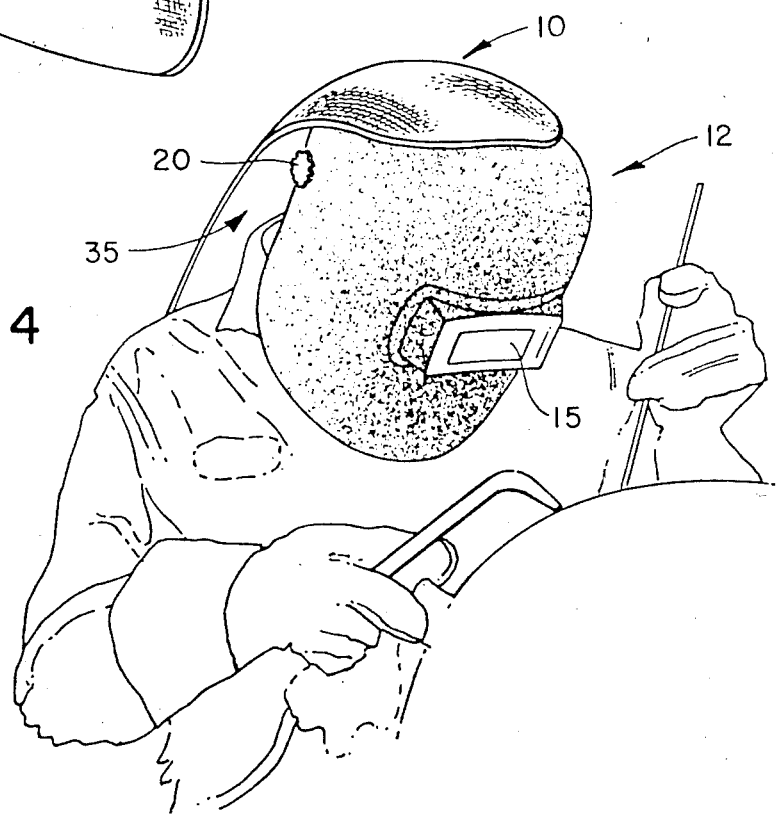
FIG. 4 is a perspective view of the protective veil and helmet from the front quarter showing the elongate side openings oriented in the forward direction between the helmet and the veil.

Referring to FIGS. 1, 3 and 4, the protecting veil or flap 10 according to the invention is mounted on and secured to a standard welding helmet 12. The welding helmet is typically a molded plastic or fiber glass face cover 14 with a dark glass viewing port 15 in the front. The welding helmet 12 is open at the top and the back with a defined helmet edge contour 16 across the top of the helmet. The helmet is supported on the head of a welder by head gear comprising straps 17 and 18 coupled to the helmet at pivot points 20 for raising and lowering the helmet.

Figure 2:
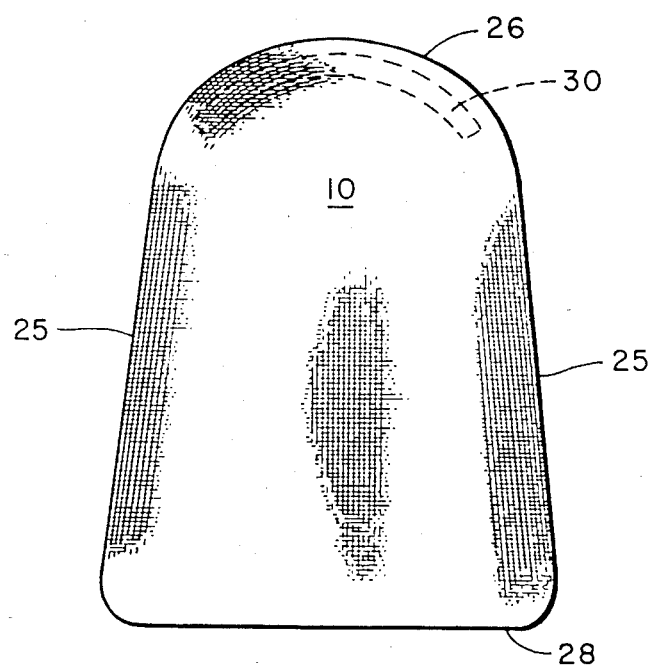
FIG. 2 is a plan view of the protective veil for retrofitting standard welding helmets according to the present invention.

The elongate veil or flap 10 shown separately in plan view in FIG. 2 is formed of a relatively lightweight flexible fire resistant fabric material such as ROXEL (TM) "flame safe" fabric having a width across the top sufficient to match the width of the welding helmet and a veil top contour 26 generally similar to the helmet edge contour 16 across the top of the helmet. Another example of a suitable fabric material is PREOX "P15" (TM) non-asbestos fire resistant fabric having a weight in the desired range of approximately 15 oz. (0.43 kg), manufactured by Steel Grip Safety Apparel Co., Inc., 700 Garfield Street, Box 833, Danville, Ill. 61832.

The lightweight fire retardant cloth composing the veil 10 is hemmed around the side edges 25, bottom edge 28 and top contour 26. Generally, the veil is constructed and arranged with reference to a standard welding helmet to eliminate all passageways and traps for welding spatter or slag. The veils are portable and foldable on the one hand and on the other hand in quantity may be stored by stacking so that they occupy little space.

For a typical standard welding helmet the protective veil or flap 10 is formed with a width across the top of the veil of 10 to 12 inches (25 to 30 cm), for example, 11 inches (27.5 cm). The veil top contour 26 may be, for example, a substantially circular arc of approximately 100° with a radius of curvature of 6 inches (15 cm) to match the curve or arc of the helmet edge contour 16 of substantially the same radius of curvature.

The veil 10 is formed with sufficient length in the range of 16 to 18 inches (42 to 45 cm) so that the veil extends over the opening at the top of the helmet and over the back of the helmet to below the bottom of the helmet 12 a sufficient distance so that the bottom of the veil may lie on the back of the shoulders of a welder wearing the welding helmet. The veil 10 is tapered with increasing width in the elongate direction from the veil top edge 26 to the bottom 28 of the veil. The bottom edge 28 is substantially wider than the top edge 26 and the helmet 12 for spreading out on either side behind the helmet across the back of the shoulders of a welder wearing the helmet. The bottom edge 28 is formed with a width in the range of 13 to 15 inches (32.5 to 37.5 cm), for example, 14 inches (35 cm).

As further shown in FIG. 2, the veil 10 is fitted with an engaging coupling surface 30 in the form of an arc of continuous coupling surface material such as VELCRO (TM) material loops or complementary hooks. The arc 30 follows the top edge contour 26 through the arc of, for example, 100° with substantially the same radius of curvature and is provided with a width of, for example, 1 inch (2.5 cm) adequate to mount and hold the veil securely to the top of the helmet.

As shown in the cross section of FIG. 1 and the cutaway of FIG. 3, the standard welding helmet 12 is retrofitted with a complementary coupling surface 32 secured in a similar arc on the outside surface of the helmet across the top of the helmet adjacent to the helmet edge contour 16. The complementary helmet coupling surface 32 is similarly formed of a continuous coupling surface material such as VELCRO (TM) complementary hooks or loops complementary with the engaging coupling surface 30 formed across the veil top edge 26. The veil 10 may therefore be rapidly deployed by mounting and securing to the top of the helmet when environmental conditions require.

According to the invention the veil 10 is not secured at the sides 25 of the veil 10 to the helmet 12. Rather, the veil and helmet coupling is constructed and arranged for free movement of the sides 25 and bottom 28 of the veil 10 relative to the back of the shoulders of a welder during movement of the welder's head and during raising and lowering of the helmet around the pivot point 20. At all times, nevertheless, and during all positions of the head of the welder and during raising and lowering of the helmet, the veil 10 protects the back of the head, neck and collar of the welder shielding and deflecting rays and spatter which may originate from above or behind.

By this construction and arrangement the protective veil at the same time permits free air movement and movement of sound waves through the helmet at side openings between the helmet and veil. As more clearly visible in FIG. 4 the elongate side openings 35 are always oriented in the forward direction between the helmet 12 and the veil 10 on a welder wearing the helmet. As a result free air movement and movement of sound waves without obstruction is preserved while still performing the protective shielding function of shielding and deflecting rays and spatter originating from above and behind.

Another advantage of the coupling between the helmet and veil, according to the present invention, is that by reason of the overlap of the veil 10 over the top of the helmet 12 there is a forward shedding of any material directed on the top of the helmet and veil from above or behind. Furthermore, because of the continuous surface coupling between the veil 10 and helmet 12 between the complementary coupling surfaces 30 and 32 across the top of the helmet, any welding spatter or material originating in front of the helmet cannot enter between the veil and helmet across the top of the helmet. The veil 10 provides a number of additional advantages for use under different conditions. The veil spread out across the back of the shoulders of a welder stops sunlight glare from entering the hood or helmet from behind relfecting off the dark glass viewing port inside and interfering in the welding operation. During outdoor arc welding the veil 10 also stops snow and rain from entering the helmet.

A significant feature and advantage of the helmet veil invention is the protection it affords welders who wear corrective eyeglasses. With conventional welding helmets, eyeglasses are subject to pitting from welding spatter, requiring frequent and costly replacement. According to the present invention, the veil protects the eyeglasses from burning slag or spatter which may enter from behind thereby extending the life of the eyeglasses and saving on replacement. This recurring problem for welders is eliminated.

The protective veil or flap when not in use or not required may be rapidly and readily removed, folded and stored in a small space such as the pocket of the welder's work clothes for later deployment and use. The protective veil or flap is not cumbersome or bulky, does not add significant extra weight to the helmet, and is comfortable to wear. There is no interference in air movement and hearing which occurs with conventional hood enclosures and no special air or cooling equipment is required.

While the invention has been described with reference to the particular preferred example embodiment, it is intended to cover all variations and equivalents within the scope of the following claims.

We claim:

1. Apparatus for protecting a welder in association with a welding helmet of the type which is open at the top and back of the helmet with a defined helmet edge contour across the top of the helmet, said helmet supported by head gear for seating over the head of the welder and for raising and lowering the helmet, comprising:

elongate flexible fabric veil means comprising fire resistant fabric material, said veil means having a width across the top sufficient to match the width of the welding helmet, and a veil top contour similar to the helmet edge contour across the top of the helmet:

said veil means formed with shoulder length for extending from the helmet edge contour across the top of the helmet over the back of the helmet and below the bottom of the helmet a sufficient distance so that the bottom of the veil means lies on the back of the shoulders of a welder wearing the welding helmet;

said veil means constructed and tapered with increasing width in the elongate direction along the sides of the veil from the veil top edge to the bottom of the veil means, said veil means having a veil bottom edge substantially wider than the helmet for spreading out on either side behind the helmet across the back of the shoulders of a welder wearing the helmet thereby deflecting arc rays, light rays, and welding spatter coming from behind the welder and shielding the welder from entry of rays or spatter into the helmet from behind:

said veil means formed with an engaging coupling surface across the veil top edge:

complementary helmet coupling surface means constructed and arranged to be secured adjacent to the helmet edge contour on the outside surface of the helmet across the top of the helmet for removably and replaceably securing the engaging coupling surface of the veil top edge to the helmet along the complementary helmet coupling surface means at the helmet edge contour on the outside surface of the top of the helmet, said veil means being secured to the top of the helmet without being secured at the sides of the veil means to the helmet:

said veil means thereby providing elongate side openings oriented in the forward direction between the helmet and the veil means on a welder wearing the helmet, for free movement of the veil means relative to the back of the shoulders of a welder during movement of the welder's head and during raising and lowering of the helmet, while protecting the back of the head, neck and collar of the welder and shielding and deflecting rays and spatter from behind, said veil means at the same time permitting free air movement and movement of sound waves through the helmet at the side openings between the helmet and veil;

said veil means being readily removable and replaceable with respect to the welding helmet and foldable and portable so that a welder can conveniently carry the veil in folded condition for ready use according to the environmental conditions at the work place.

2. The apparatus of claim 1 wherein the length of the veil means is selected in the range of from 16 to 18 inches (40 to 45 cm).

3. The apparatus of claim 1 wherein the tapered width of the veil means is selected to be in the range from approximately 10 inches to 15 inches (25 to 38 cm).

4. The apparatus of claim 1 wherein the helmet edge contour across the top of the helmet comprises an arc of a specified radius of curvature and wherein the veil top edge also comprises an arc of the same radius of curvature.

5. The apparatus of claim 1 wherein the engaging coupling surface across the veil top edge and the complementary helmet coupling surface secured across the helmet edge contour on the outside surface across the top of the helmet comprises a continuous coupling seal across the top of the helmet for deflecting rays and spatter without permitting entry through the seal between the veil means and the top of the helmet.

6. The apparatus of claim 5 wherein the helmet edge contour across the top of the helmet comprises an arc of a specified radius of curvature and wherein the veil top edge also comprises an arc of the same radius of curvature.

7. The apparatus of claim 6 wherein the engaging coupling surface across the veil top edge and the complementary helmet coupling surface across the top of the helmet comprise arcs of substantially the same radius of curvature as the veil top edge and the helmet edge contour.

* * * * *

UNITED STATES PATENT AND TRADEMARK OFFICE
CERTIFICATE OF CORRECTION

PATENT NO. : 4,556,991

DATED : December 10, 1985

INVENTOR(S) : Mihail A. Margaronis, et al

It is certified that error appears in the above-identified patent and that said Letters Patent is hereby corrected as shown below:

On the title page Item [76] Inventors: "Bangor, Mass." should read -- Bangor, Me. --.

Signed and Sealed this

Ninth Day of September 1986

[SEAL]

Attest:

Attesting Officer

DONALD J. QUIGG

Commissioner of Patents and Trademarks